United States Patent
Karni

(10) Patent No.: US 10,945,792 B2
(45) Date of Patent: Mar. 16, 2021

(54) LASER SYSTEM AND METHOD

(71) Applicant: Zlasers Ltd., Kfar Shemaryahu (IL)

(72) Inventor: Ziv Karni, Kfar Shemaryahu (IL)

(*) Notice: Subject to any disclaimer, the term of this patent is extended or adjusted under 35 U.S.C. 154(b) by 150 days.

(21) Appl. No.: 16/106,375

(22) Filed: Aug. 21, 2018

(65) Prior Publication Data
US 2020/0060763 A1    Feb. 27, 2020

(51) Int. Cl.
*A61B 18/20* (2006.01)
*A61B 17/00* (2006.01)
*A61B 18/00* (2006.01)

(52) U.S. Cl.
CPC .. *A61B 18/203* (2013.01); *A61B 2017/00769* (2013.01); *A61B 2018/00452* (2013.01)

(58) Field of Classification Search
CPC .......... A61B 18/20; A61B 18/203; A61B 2018/2035; A61B 2018/20351; A61B 2018/20353; A61B 2018/20355; A61B 2018/20359; A61B 2018/20361; A61B 2018/00452; A61B 2018/00458; A61B 2018/0047; A61B 2018/00571; A61B 2018/00577; A61B 2018/00636; A61B 2018/00642; A61B 2018/00648; A61B 2018/00654; A61B 2018/00666; A61B 2018/00773; A61B 2018/00791; A61B 2018/00904; A61B 2017/00743; A61B 2017/00747; A61B 2017/00756; A61B 2017/00761; A61B 2017/00769; A61B 2017/00744
USPC .......... 606/9–13, 17–20, 22, 23; 607/88, 89; 128/898
See application file for complete search history.

(56) References Cited

U.S. PATENT DOCUMENTS

| | | | |
|---|---|---|---|
| 6,015,404 A * | 1/2000 | Altshuler | A61B 18/203 606/10 |
| 2008/0033410 A1* | 2/2008 | Rastegar | A61B 18/20 606/9 |
| 2008/0058783 A1 | 3/2008 | Altshuler | |
| 2008/0247637 A1 | 10/2008 | Gildenberg | |
| 2014/0005756 A1* | 1/2014 | Liu | A61N 5/0616 607/90 |
| 2015/0032092 A1* | 1/2015 | Adanny | A61B 18/203 606/9 |
| 2016/0192961 A1* | 7/2016 | Ginggen | A61B 17/3203 604/173 |
| 2017/0215962 A1 | 8/2017 | Aharon | |

FOREIGN PATENT DOCUMENTS

EP    0880941    12/1998

OTHER PUBLICATIONS

PCT Search Report and Written Opinion PCT/IB2019/056921, dated Nov. 27, 2019.

* cited by examiner

*Primary Examiner* — Ahmed M Farah
(74) *Attorney, Agent, or Firm* — Dekel Patent Ltd.; David Klein

(57) ABSTRACT

A method for pigment removal from skin includes sensing properties of a pigmented area of skin with a camera, communicating the properties to a controller, and sending commands from the controller to a laser system to scan the pigmented area in a random pattern with laser beams of different wavelengths in accordance with the properties so as to remove a portion of pigment from the pigmented area.

8 Claims, 1 Drawing Sheet

LASER SYSTEM AND METHOD

FIELD OF THE INVENTION

The present invention generally relates to a system and method for lightening or eradicating pigments in human skin, such as tattoos or pigmented skin lesions, with laser energy.

BACKGROUND OF THE INVENTION

Extremely short pulse (ESP) nanosecond or picosecond laser systems can successfully lighten or eradicate a variety of pigmented lesions, such as selectively destroying tattoo pigment without causing much damage to the surrounding skin. The altered pigment is then removed from the skin by scavenging white blood cells and tissue macrophages.

Q-switching can produce light pulses with extremely short (in the range of nanoseconds) pulse duration and high (megawatt) peak power, much higher than can be produced by the same laser operating in continuous wave mode (constant output), or free-running pulse mode (0.1 ms-300 ms). Laser pulses can also be in the range of picoseconds. The ESP laser systems are effective because they confine their energy to the treated pigments. The time duration (pulse duration) of the ESP laser energy is so short that the extremely small pigments of a size of 10 nm-100 nm are heated to fragmentation temperature before their heat can dissipate to the surrounding skin. This prevents heating of the surrounding tissue that could potentially lead to burning or scarring of the skin.

The most likely cause of pigment destruction when subjecting the pigments to ESP laser pulses are shockwave and/or cavitation damage, the photomechanical physical effects produced from thermal expansion, and/or the extreme temperature gradients created within the melanosome or tattoo pigment. For the selective removal of pigment, the color of the laser light must penetrate far enough into the skin to reach the target pigment and must be highly absorbed by the pigment relative to the surrounding skin. Different pigments therefore require different laser colors. For example, 532 nm and near-infrared 1064 nm are commonly used wavelengths. Commonly used parameters are around 5-10 $J/cm^2$ in order to be effective with a spot size of 2-4 mm.

The treatment is done manually by moving the laser spot along the specific color of the tattoo and the complementary wavelength of the laser.

However, the treatment is associated with some degree of pain mainly due to the absorption of the laser energy and the density of the spots, which are usually done one near the other. In addition, the treatment is quite slow. Although most of the lasers can work at 10 pulses per second (pps), the common pulse repetition rate is much smaller in order to alleviate pain and to allow comfortably moving the laser beam over the contour of the tattoo by hand.

SUMMARY OF THE INVENTION

The present invention seeks to provide a novel and improved system and method for lightening or eradicating pigments in human skin, such as tattoos or pigmented skin lesions, with laser energy, as described in detail below. The examples described herein are for tattoo removal but the invention can be used for any skin pigment removal. For example, pigmented lesions that are treatable with the invention include, without limitation, freckles and birthmarks including congenital melanocytic nevi, blue nevi, nevi of Ota/Ito and Becker nevi.

Other applications of the invention include, without limitation, vascular applications. For example, small varicose veins may be treated with laser pulses at multiple locations. The system of the invention may be used to sense and monitor the contour of the vascular vein and irradiate it with laser pulses, such as but not limited to, laser pulses up to 200 $J/cm^2$ with wavelengths such as 1064 or 532 nm for small veins.

The pigment removal laser cooperates with a CCD camera having high resolution and an image processor. The high resolution CCD camera views the tattoo or other pigment which is to be removed. The camera may be integrated into a laser scanner.

Two marks on the patient skin may be used as fiducial marks that enable the camera to identify the exact location of the tattoo and compensate for any movement of the patient in real time.

Controller software allows the laser to remove the tattoo of a specific color; afterwards the laser system changes the output wavelength in accordance with the pigment as sensed by the camera and the procedure repeats itself until all pigments are lightened or eradicated.

The software controls the repetition rate of the lasers and synchronizes the operation of the laser with the scanner.

The spots of the laser on the tissue can be randomly applied on the tattoo contour to avoid shooting adjacent spots. This synergistically reduces pain while at the same time enables using the maximum repetition rate of the laser.

In an embodiment of the invention, multiple laser beams of different wavelengths may emanate from multiple directions and be directed to a single focal spot. This allows quick switching between different wavelengths.

In an embodiment of the invention, cooling methods can be used to cool the treated area and thus alleviate pain.

There is thus provided in accordance with a non-limiting embodiment of the present invention a method for pigment removal from skin including sensing properties of a pigmented area of skin with a camera, communicating the properties to a controller, and sending commands from the controller to a laser system to scan the pigmented area in a random pattern with laser beams of different wavelengths in accordance with the properties so as to remove a portion of pigment from the pigmented area.

The properties may include color and boundaries of the pigmented area.

In accordance with a non-limiting embodiment of the present invention the camera senses fiducial marks associated with the pigmented area, and if during scanning the pigmented area moves relative to the fiducial marks, the laser beams are moved such that the laser beams impinge on the pigmented area.

In accordance with a non-limiting embodiment of the present invention sending commands includes commanding a first laser to emit a laser beam with a first wavelength on the pigmented area, and upon reaching a color threshold target or a maximum allowable skin temperature, ceasing output of the first laser and switching to another laser with a different wavelength.

In accordance with a non-limiting embodiment of the present invention the pigmented area may be scanned with multiple laser beams of different wavelengths emanating from multiple directions and directed to a single focal spot. The pigmented area may be cooled before, during or after scanning with the laser beams.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
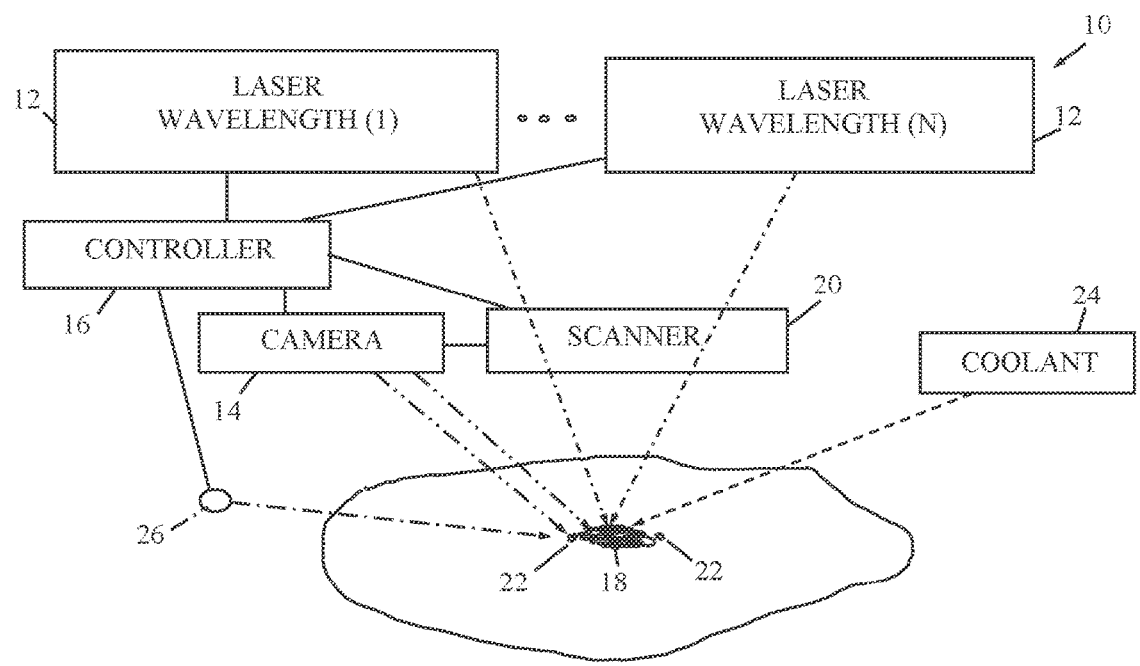
FIG. 1 is a simplified illustration of a pigment removal laser system, constructed and operative in accordance with a non-limiting embodiment of the present invention.
Figure 2:
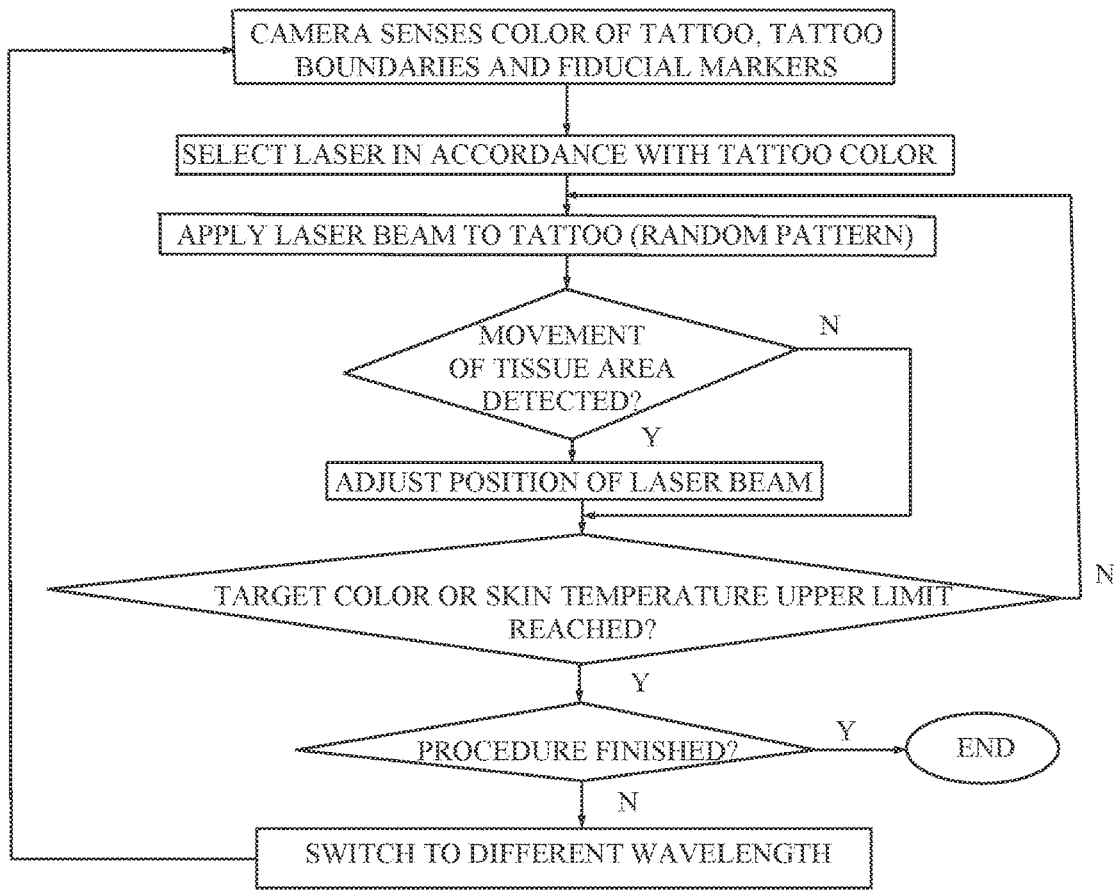
FIG. 2 is a simplified block diagram of a method for using the system of FIG. 1, in accordance with a non-limiting embodiment of the present invention.

Reference is now made to FIG. 1, which illustrates a pigment removal laser system 10, constructed and operative in accordance with a non-limiting embodiment of the present invention.

System 10 includes lasers 12 of different wavelengths for removing pigments of different colors. For example, lasers 12 may include Q-switched Nd:YAG lasers (e.g., 532 nm frequency-doubled Nd:YAG laser), red light lasers (e.g., 694 nm ruby, 755 nm alexandrite), and near-infrared lasers (e.g., 1064 nm Nd:YAG)). The energy flux may be, without limitation, 5-10 J/cm$^2$ for a spot size of 2-4 mm.

The lasers 12 cooperate with a camera 14, such as a CCD camera having high resolution, and an image processor (controller) 16. The high resolution CCD camera 14 views the tattoo or other pigment 18 which is to be removed. The camera 14 may be integrated into a laser scanner 20, such as but not limited to, a digital galvo-scanner with a clear aperture of 5-15 mm. The camera 14 senses the pigment color and the particular laser wavelength is chosen by controller 16.

Two marks on the patient skin may be used as fiducial marks 22 that enable the camera 14 to identify the exact location of the tattoo 18, and if movement is detected, to adjust the position of the laser beam to compensate for any movement of the patient in real time such that the laser beam still impinges on the pigmented area to be treated.

The lasers 12 are operatively coupled to the scanner 20 and controlled by controller 16 that has image processing software that moves the scanner 20 (such as an XY galvo-scanner) according to the contour and the color of the tattoo 18. The image processing software of controller 16 controls the application of the laser beams to lighten or remove the tattoo of a specific color. The camera 14 provides feedback to the controller 16 regarding the change in color of the tattoo 18. A temperature sensor 26 (such as, but not limited to, a non-contact thermal radiation sensor) may provide feedback to the controller 16 regarding skin temperature. Upon reaching a color threshold target or maximum allowable skin temperature, the controller 16 ceases output of the currently used laser and then switches to another laser with a different wavelength in accordance with the pigment as sensed by the camera 14. The procedure repeats itself until all pigments are lightened or eradicated.

The software of controller 16 controls the repetition rate of the lasers 12 and synchronizes the operation of the lasers 12 with the scanner 20.

The software of controller 16 controls application of the laser beams so that the laser beams are randomly applied on the tattoo contour to avoid shooting beams on adjacent spots. This synergistically reduces pain while at the same time enables using the maximum repetition rate of the laser (e.g., 10 pps).

The treatment area can be small (e.g., a few square centimeters) or large (e.g., 300 cm$^2$). The distance of the scanner 20 from the tissue can be, without limitation, 10-50 cm, depending on the particular need.

In an embodiment of the invention, multiple laser beams of different wavelengths can emanate from multiple directions and may be directed to a single focal spot. This allows quick switching between different wavelengths.

In an embodiment of the invention, a coolant 24 can be applied at the laser spot to cool the treated area and thus alleviate pain. Cooling can be achieved before, during or after laser treatment, referred to as pre-cooling, parallel cooling and post-cooling, respectively. Coolant 24 can cool the area by conduction, convection and/or radiation. Examples of conduction cooling include, without limitation, metal or sapphire tips, ice or cold gels, or thermoelectric cooling. Examples of convection cooling include, without limitation, fluid convection with liquid or gas, or cryogenic sprays.

What is claimed is:

1. A method for pigment removal from skin comprising:
   sensing properties of a pigmented area of skin with a camera;
   communicating said properties to a controller;
   sending commands from said controller to a laser system to scan said pigmented area in a random pattern with laser beams of different wavelengths in accordance with said properties so as to remove a portion of pigment from said pigmented area; and
   scanning said pigmented area with multiple laser beams of different wavelengths emanating from multiple directions and directed to a single focal spot.

2. The method according to claim 1, wherein said properties comprise color and boundaries of said pigmented area.

3. The method according to claim 1, wherein said camera senses fiducial marks associated with said pigmented area, and if during scanning said pigmented area moves relative to said fiducial marks, causing said laser beams to move such that said laser beams impinge on said pigmented area.

4. The method according to claim 1, wherein sending commands comprises commanding a first laser to emit a laser beam with a first wavelength on said pigmented area, and if a predefined color threshold target or a predefined maximum allowable skin temperature is reached with said first laser, then ceasing output of said first laser and switching to another laser with a different wavelength.

5. The method according to claim 1, comprising cooling said pigmented area before, during or after scanning with said laser beams.

6. The method according to claim 1, wherein said pigmented area comprises a tattoo.

7. The method according to claim 1, wherein said random pattern of laser beams of different wavelengths does not apply said laser beams on adjacent spots on said area of the skin.

8. The method according to claim 1, further comprising increasing a repetition rate of laser pulses from said laser system and simultaneously using said repetition rate of laser pulses to reduce pain.

\* \* \* \* \*